US008367615B2

(12) United States Patent
Filbin et al.

(10) Patent No.: US 8,367,615 B2
(45) Date of Patent: Feb. 5, 2013

(54) STIMULATION OF NEURON REGENERATION BY SECRETORY LEUKOCYTE PROTEASE INHIBITOR

(75) Inventors: Marie T. Filbin, New York, NY (US); Sari S. Hannila, New York, NY (US)

(73) Assignee: Research Foundation of City University of New York, New York, NY (US)

( * ) Notice: Subject to any disclaimer, the term of this patent is extended or adjusted under 35 U.S.C. 154(b) by 448 days.

(21) Appl. No.: 12/225,639

(22) PCT Filed: Mar. 30, 2007

(86) PCT No.: PCT/US2007/008270
§ 371 (c)(1),
(2), (4) Date: Jun. 16, 2010

(87) PCT Pub. No.: WO2007/117440
PCT Pub. Date: Oct. 18, 2007

(65) Prior Publication Data
US 2010/0256065 A1    Oct. 7, 2010

Related U.S. Application Data

(60) Provisional application No. 60/787,927, filed on Mar. 31, 2006, provisional application No. 60/788,021, filed on Mar. 30, 2006.

(51) Int. Cl.
*A61K 38/57* (2006.01)
(52) U.S. Cl. .................................. 514/17.7; 514/20.3
(58) Field of Classification Search .................. None
See application file for complete search history.

(56) References Cited

U.S. PATENT DOCUMENTS

| | | | |
|---|---|---|---|
| 5,762,926 A | 6/1998 | Gage et al. | |
| 5,932,542 A | 8/1999 | Filbin | |
| 5,981,225 A | 11/1999 | Kochanek et al. | |
| 6,017,880 A * | 1/2000 | Eisenberg et al. | 514/3.8 |
| 6,096,716 A | 8/2000 | Hayes et al. | |
| 6,180,613 B1 | 1/2001 | Kaplitt et al. | |
| 6,203,792 B1 | 3/2001 | Filbin | |
| 6,210,664 B1 | 4/2001 | Cherksey et al. | |
| 6,399,577 B1 | 6/2002 | Filbin | |
| 2002/0064873 A1 | 5/2002 | Yang et al. | |
| 2002/0164309 A1 | 11/2002 | Carpenter | |
| 2002/0168338 A1 | 11/2002 | Baird | |
| 2002/0168760 A1 | 11/2002 | Dornburg et al. | |
| 2009/0232910 A1* | 9/2009 | Schmechel et al. | 424/722 |

FOREIGN PATENT DOCUMENTS

| | | |
|---|---|---|
| WO | WO 97/01352 | 1/1997 |
| WO | WO 97/32608 | 9/1997 |
| WO | WO 00/08192 | 2/2000 |
| WO | WO 01/03719 | 1/2001 |
| WO | WO 01/85981 | 11/2001 |
| WO | WO 02/50287 | 6/2002 |

OTHER PUBLICATIONS

Ashcroft et al., "Secretory leukocyte protease inhibitor mediates non-redundant functions necessary for normal wound healing," *Nature Medicine*, 6(10):1147-1153 (2000).
Carlson et al., "Acute inflammatory response in spinal cord following impact injury," *Experimental Neurology*, 151(1):77-88 (1998).
Chen et ah, "Nogo-A is a myelin-associated neurite outgrowth inhibitor and an antigen for monoclonal antibody IN-1," *Nature*, 403(6768):434-439 (2000).
Domeniconi et al., "Myelin-associated glycoprotein interacts with the Nogo66 receptor to inhibit neurite outgrowth," *Neuron*, 35:283-290 (2002).
Elliott, "Cytokine upregulation in a murine model of familial amyotrophic lateral sclerosis," *Molecular Brain Research*, 95(1-2):172-178 (2001).
Fournier et al., "Identification of a receptor mediating Nogo-66 inhibition of axonal regeneration," *Nature*, 409(6818):341-346 (2001).
GrandPre et al., "Identification of the Nogo inhibitor of axon regeneration as a Reticulon protein," *Nature*, 403:439-444 (2000).
GrandPre et al., "Nogo-66 receptor antagonist peptide promotes axonal regeneration," *Nature*, 417(6888):547-551 (2002).
Grütter et al., "The 2.5 A X-ray crystal structure of the acid-stable proteinase inhibitor from human mucous *secretions analysed in its complex with bovine alpha-chymotrypsin*," The EMBO Journal, 7(2):345-351 (1988).
Ilzecka et al., "Increased serum levels of endogenous protectant secretory leukocyte protease inhibitor in acute ischemic stroke patients," *Cerebrovascular Diseases*, 13(1):38-42 (2002).
Jin et al., "Secretory leukocyte protease inhibitor: a macrophage product induced by and antagonistic to bacterial lipopolysaccharide," *Cell*, 88(3):417-426 (1997).
Liu et al., "Myelin-associated glycoprotein as a functional ligand for the Nogo-66 receptor," *Science*, 297(5584):1190-1193 (2002).
Ma et al.,"Secretory leukocyte protease inhibitor binds to annexin II, a cofactor for macrophage HIV-1 infection," *Journal of Experimental Medicine*, 200(10):1337-1346 (2004).
Masuda et al., "Pharmacological activity of the C-terminal and N-terminal domains of secretory leukoprotease inhibitor in vitro," *British Journal of Pharmacology*, 115(6):883-888 (1995).
McKerracher et al., "Identification of myelin-associated glycoprotein as a major myelin-derived inhibitor of neurite growth," *Neuron*, 13(4):805-811 (1994).
Mukhopadhyay et al., "A novel role for myelin-associated glycoprotein as an inhibitor of axonal regeneration," *Neuron*, 13(3):757-767 (1994).

(Continued)

*Primary Examiner* — Robert C Hayes
(74) *Attorney, Agent, or Firm* — Fish & Richardson P.C.

(57) ABSTRACT

The present invention provides methods for stimulating neuronal survival, growth and regeneration by administering SLPIs to animals, such as humans. These methods can be used to treat a variety of neurological conditions such as neural injuries and degenerative diseases in subjects in need thereof.

8 Claims, 8 Drawing Sheets

OTHER PUBLICATIONS

Mulligan et al., "Anti-inflammatory effects of mutant forms of secretory leukocyte protease inhibitor," *American Journal of Pathology*, 156(3):1033-1039 (2000).

Norton et al., "Myelination in rat brain: method of myelin isolation," *Journal of Neurochemistry*, 21(4):749-757 (1973).

Qiu et al., "Spinal axon regeneration induced by elevation of cyclic AMP," *Neuron*, 34(6):895-903 (2002).

Taggart et al., "Secretory leucoprotease inhibitor binds to NF-kappaB binding sites in monocytes and inhibits p65 binding," *Journal of Experimental Medicine*, 202(12):1659-1668 (2005).

Taoka et al., "Role of neutrophil elastase in compression-induced spinal cord injury in rats," *Brain Research*, 799(2):264-269 (1998).

Taoka et al., "Role of neutrophils in spinal cord injury in the rat," *Neuroscience*, 79(4):1177-1182 (1997).

Tortarolo et al., "Persistent activation of p38 mitogen-activated protein kinase in a mouse model of familial amyotrophic lateral sclerosis correlates with disease progression," *Molecular and Cellular Neuroscience*, 23(2):180-192 (2003).

Wang et al., "Up-regulation of secretory leukocyte protease inhibitor (SLPI) in the brain after ischemic stroke: adenoviral expression of SLPI protects brain from ischemic injury," *Molecular Pharmacology*, 64(4):833-840 (2003).

Wang et al., "Oligodendrocyte-myelin glycoprotein is a Nogo receptor ligand that inhibits neurite outgrowth," *Nature*, 417(6892):941-944 (2002).

Yuasa et al., "Tumor necrosis factor signaling to stress-activated protein kinase (SAPK)/Jun NH2-terminal kinase (JNK) and p38. Germinal center kinase couples TRAF2 to mitogen-activated protein kinase/ERK kinase kinase 1 and SAPK while receptor interacting protein associates with a mitogen-activated protein kinase kinase kinase upstream of MKK6 and p38," *Journal of Biological Chemistry*, 273(35):22681-22692.

* cited by examiner

STIMULATION OF NEURON REGENERATION BY SECRETORY LEUKOCYTE PROTEASE INHIBITOR

This application is a national stage application under 35 U.S.C. §371 of International Patent Application No. PCT/US2007/008270, filed Mar. 30, 2007, which claims priority from U.S. Provisional Patent Application Nos. 60/787,927, filed Mar. 31, 2006, and 60/788,021, filed Mar. 30, 2006. The disclosures of all the aforementioned priority applications are incorporated by reference in their entirety herein.

TECHNICAL FIELD OF THE INVENTION

This invention relates to the use of secretory leukocyte protease inhibitor to stimulate neural survival, growth and regeneration in animals, e.g., humans.

BACKGROUND OF THE INVENTION

The mammalian nervous system does not regenerate after injury despite the fact that there are many molecules present which encourage/promote axonal (nerve) growth. There are at least three factors that are responsible for this lack of regeneration: the formation of a glial scar, the presence of inhibitors of regeneration in myelin, and the intrinsic growth capacity of adult axons. In situations involving injury, the glial scar takes some time after injury to form. It would be advantageous to encourage axonal growth during this "window-of-opportunity", before the scar forms. It would also be desirable to be able to encourage axonal growth irrespective of scarring, e.g., for treating or preventing neural degeneration or damage associated with a disorder, disease or condition. Blocking the function of the inhibitors of regeneration present in myelin can be achieved by, e.g., neutralizing the inhibitors or altering the growth capacity of the axon so that it no longer responds to the inhibitors.

To date, three inhibitors have been identified in myelin: myelin-associated glycoprotein ("MAG") (McKerracher et al., Neuron 13:805-11 (1994); Mukhopadhyay et al., Neuron 13: 757-67 (1994); U.S. Pat. No. 5,932,542, U.S. Pat. No. 6,203,792, and U.S. Pat. No. 6,399,577; and WO 97/01352), Nogo (Chen et al., Nature 403:434-439 (2000); Grandpre et al., Nature 403:439-444 (2000)); and oligodendrocyte myelin glycoprotein ("Omgp") (Wang et al., Nature 417:941-944 (2002)). All three of these inhibitors bind to Nogo-66 receptor ("NgR") to exert their inhibitory effects (Wang et al., supra; Domeniconi et al., Neuron 35:283-290 (2002); Fournier et al., Nature 409:341-346 (2001); Liu et al., Science 297:1190-1193 (2002)).

It has been shown that by raising levels of a cyclic nucleotide called cyclic adenosine monophosphate ("cAMP"), one can reduce the inhibitory effects of MAG and significantly improve nerve fiber growth (WO 01/85981).

SUMMARY OF THE INVENTION

We have made the surprising discovery that cAMP greatly increases the production of secretory leukocyte protease inhibitor ("SLPI"); and that SLPI overcomes the inhibitory effect of myelin inhibitors on nerve fiber growth and promotes neuronal (e.g., axonal) regeneration. Before our discovery, it was not known that SLPI possesses neuro-stimulatory function.

Accordingly, the present invention provides methods described in the following paragraphs for promoting neuronal survival, growth and regeneration. Because SLPI is also an anti-inflammatory agent, it is also useful in protecting secondary neuronal injury caused by inflammation.

The present invention provides a method of stimulating the axonal outgrowth of a neuron, comprising contacting the neuron with an SLPI, thereby stimulating said axonal outgrowth.

The present invention also provides a method of decreasing the NF-κB or c-jun activity in a neuron, comprising contacting the neuron with an SLPI, thereby decreasing said NF-κB or c-jun activity.

Also provided methods of decreasing the inhibition of axonal outgrowth of a neuron by myelin, comprising contacting the neuron with an SLPI, thereby decreasing said inhibition.

In each of the above embodiments the contacting step may comprise contacting the cell body or contacting the axon of the neuron with SLPI. In some embodiments the neuron is injured. The neuron may be a central nervous system, e.g., spinal cord or peripheral nervous system neuron. In some embodiments the neuron may be a motor neuron.

The present invention also provides a method of stimulating neural growth or regeneration in the nervous system in a patient, comprising administering to the patient a composition comprising SLPI. Also provided are a method of treating injuries or neural tissue damage in a patient, comprising administering to the patient a composition comprising SLPI. The present invention also provides a method of treating or preventing neural degeneration or damage associated with a disease, disorder or condition in a patient, comprising administering to the patient a composition comprising SLPI. In some embodiments of the methods of the invention the patient suffers from neural disease, disorder or injury including, but not limited to, spinal cord injury, Alzheimer's disease, Parkinson's disease, Huntington's disease, multiple sclerosis, Creutzfeldt-Jacob's disease, kuru, multiple system atrophy, progressive supranuclear palsy, aneurysm, non-ischemic cranial or cerebral trauma, peripheral nerve injury, neuropathy, demyelinating disease, ALS, Charcot-Marie-Tooth diseases, or spinal motor atrophy.

Other features and advantages of the invention will be apparent from the following detailed description and figures.

DETAILED DESCRIPTION OF THE INVENTION

Figure 1A:
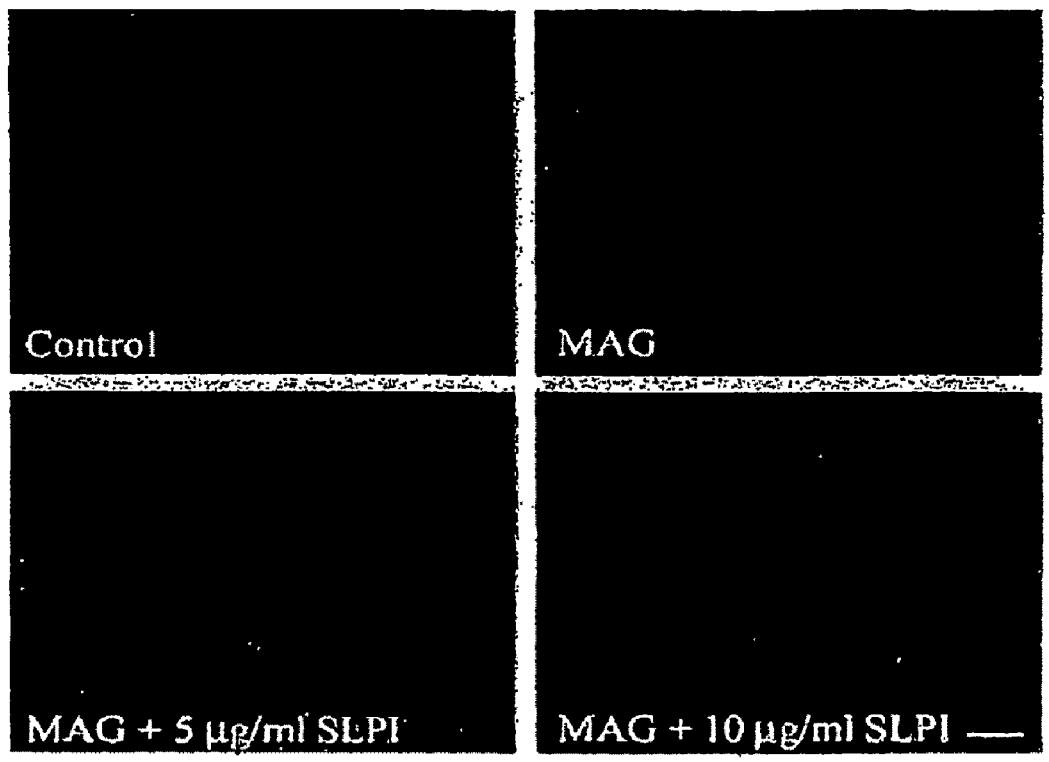
FIGS. 1A and 1B are a panel of four photographs and a bar graph, respectively, showing that SLPI reverses inhibition by MAG for dorsal root ganglia ("DRG") neurons. DRG neurons from post-natal day 6 rats were treated with 2, 5, or 10 µg/ml SLPI, plated onto monolayers of either control or MAG-expressing Chinese hamster ovary ("CHO") cells, and incubated for 16 hours. Neurons were stained for βIII tubulin and neurite length was quantified using the METAMORPH image analysis software. Data are presented ±SEM.

SLPI is a potent inhibitor of leukocyte serine proteases such as elastase and cathepsin G from neutrophils, and chymase and tryptase from mast cells, as well as trypsin and chymotrypsin from pancreatic acinar cells (Jin et al., Cell 88:417-26 (1997) and references cited therein; Grütter et al., The EMBO Journal 7:345-51 (1988)). SLPI has multiple functions relevant to innate host defense, including anti-inflammatory, anti-viral, anti-fungal and anti-bacterial properties. In addition, it has been found to promote cutaneous wound healing in mice (Ashcroft et al., Nature Med. 6:1147-53 (2000)). See also Wang et al., Mol. Pharma. 64:833-40 (2003).

In the immune system, SLPI has been shown to be an lipopolysaccharide (LPS)-induced, IFNγ-suppressible phagocyte product that inhibits LPS responses. SLPI binds to the membrane of human macrophages through annexin II (Jin et al., supra, and Ma et al., J. of Exp. Med. 200:1337-46 (2004)). SLPI binds to NF-κB binding sites in the promoter regions of the IL-8 and TNF-α genes in monocytes and inhibit the expression of those genes (Taggart et al., J. Exp. Med. 202:1659-68 (2005) and references cited therein). It has been suggested that the anti-inflammatory function of SLPI arises from such gene inhibition.

Recent studies suggest that SLPI may play a neuroprotective role in focal stroke because of rapid inhibition of activated proteases and its suppression in inflammatory response mediated by leukocytes (e.g., neutrophils and macrophages), which contributes to ischemic brain injury (Taggart et al., supra; Ilzecka et al., Cerebrovascular Diseases 13:38-42 (2002)). Elevated levels of serum SLPI are also observed in human stroke patients (Ilzecka et al., supra). However, it is not known what effect, if any, SLPI has on neurons themselves at the ischemic sites (Wang et al., supra).

Human SLPI is an 11.7 kDa protein found in parotid saliva, and in seminal plasma, cervical, nasal, and bronchial mucus. In human epithelial cells, SLPI is constitutively expressed and its expression is increased by phorbol ester, TNF-α, and LPS at supraphysiologic concentrations, as well as by synergistic combinations of elastase and corticosteroids (Jin et al., supra). SLPI is composed of two cysteine-rich domains with a protease inhibitory site situated at leucine 72 (human form) in the carboxy-terminal domain.

We have discovered that SLPI promotes neurite (including axonal) growth in vitro, and increase the growth capacity of neurons when it is administered in vivo. This discovery shows that SLPI will be useful in treating central nervous and peripheral system injuries, such as spinal cord injury, as well as diseases characterized by axonal degeneration. SLPI may be useful also for neural regeneration or treating or slowing the progression of neural degeneration. We have also found that SLPI may achieve its stimulatory effect by regulating gene transcription in neurons.

SLPIs Useful in the Invention

An SLPI used in the present methods can be a wildtype SLPI protein from mammals such as humans, rats, and mice, or its various homologs, allelic variants, and isoforms. The amino acid sequences of a human SLPI, a rat SLPI and a mouse SLPI are described in Wang et al., supra. See also Grütter et al., supra, for a full length human SLPI sequence and its X-ray crystal structure.

Minor variations in the amino acid sequences of SLPI also are considered to be part of the present invention, provided that the variations in the amino acid sequence maintain at least 75%, more preferably at least 80%, 90%, 95%, and most preferably 99% or more sequence identity and the molecule retains bioactivity (e.g., regulation of nerve growth and regeneration as assayed by any methods known, e.g., neurite outgrowth assays described in paragraph 35 and Example 2 below). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family.

For example, it is reasonable to expect that an isolated replacement of a leucine with an isoleucine or valine, an aspartate with a glutamate, a threonine with a serine, or a similar replacement of an amino acid with a structurally related amino acid will not have a major effect on the properties of the resulting molecule. Whether an amino acid change results in a functional peptide or protein can readily be determined by assaying the specific activity of the peptide or protein derivative using, e.g., the assays described in detail herein.

However, the SLPIs of this invention need not show high degrees of homology or sequence identity to the wildtype sequences. In fact, rat, mouse and human SLPIs do not share a high degree of homology. Rat SLPI shares only about 80% and 60% amino acid sequence identity with its mouse and human counterparts, respectively (Feuerstein, supra). However, these SLPIs share striking structural similarities (see, e.g., Jin et al., supra). Thus, when the SLPI proteins useable in this invention share a relatively low degree of sequence identity (e.g., 50%, 60%, or 70%) to known wildtype sequences, they preferably preserve amino acid residues at positions critical to the overall protein structure and function (e.g., neuro-stimulatory function, serine protease inhibition function and NF-κB inhibitory function). For example, FIG. 2 of Wang et al. shows the highly conserved cysteine and proline residues in rat, mouse and human SLPIs. Mulligan et al. (Am. J. of Path. 156:1033-39 (2000)) further shows examples of SLPI variants useful in this invention.

SLPIs useable in this invention also include fragments of a full-length SLPI that preserve the desired SLPI functions. For example, Masuda et al. (British J. of Pharma. 115:883-888 (1995)) describes a SLPI protein containing the C-terminal domain of the full length SLPI and having significant levels of the full length molecule's serine protease and NF-κB inhibitory activities.

SLPIs of this invention also include fusion proteins containing SLPI linked to a functional moiety. The functional moiety can be used to direct SLPI to the desired neuronal site, to enhance the function, including the in vivo half-life, of SLPI, or to facilitate production and purification of SLPI. For example, the moiety can be genetic, enzymatic or chemical or immunological markers such as epitope tags, myc, hemagglutinin (HA), GST, immunoglobulins, β-galactosidase, biotin trpE, protein A, β-lactamase, α-amylase, maltose binding protein, alcohol dehydrogenase, polyhistidine (for example, six histidine at the amino and/or carboxyl terminus of the polypeptide), lacZ, green fluorescent protein (GFP), yeast a mating factor, GAL4 transcription activation or DNA binding domain, luciferase, and serum proteins such as ovalbumin, albumin and the constant domain (e.g., Fc) of IgG. See, e.g., Godowski et al., 1988, and Ausubel et al., supra. Immunoglobulin Fc regions are especially useful fusion partners for making secreted fusion proteins as immunoglobulin molecules are secreted at high levels from the mature plasma cell, and the Fc region appears to be well suited as a "surrogate mother," accepting domains from other proteins and efficiently directing them through the endoplasmic reticulum and secretory pathway.

Fusion proteins may also contain sites for specific enzymatic cleavage, such as a site that is recognized by enzymes such as Factor XIII, trypsin, pepsin, or any other enzyme known in the art. Fusion proteins will typically be made by either recombinant nucleic acid methods, as described above, chemically synthesized using techniques such as those described in Merrifield, 1963, herein incorporated by reference, or produced by chemical cross-linking. Tagged fusion proteins permit easy localization, screening and specific binding via the epitope or enzyme tag. Some tags allow the protein of interest to be displayed on the surface of a phagemid, such as M13, which is useful for panning agents that may bind to the desired protein targets. Another advantage of fusion proteins is that an epitope or enzyme tag can simplify purification. These fusion proteins may be purified, often in a single step, by affinity chromatography. For example, a $His^6$ tagged protein can be purified on a Ni affinity column and a GST fusion protein can be purified on a glutathione affinity column. Similarly, a fusion protein comprising the Fc domain of IgG can be purified on a Protein A or Protein G column and a fusion protein comprising an epitope tag such as myc can be purified using an immunoaffinity column containing an anti-c-myc antibody. It is preferable that the epitope tag be separated from the protein encoded by the essential gene by an enzymatic cleavage site that can be cleaved after purification. A second advantage of fusion proteins is that the epitope tag can be used to bind the fusion protein to a plate or column through an affinity linkage for screening targets.

The SLPI proteins of this invention can be derivatized, e.g., pegylated, acetylated, carboxylated, phosphorylated, glycosylated or ubiquitinated. In some embodiments, the derivative has been labeled with, e.g., radioactive isotopes such as $^{125}I$, $^{32}P$, $^{35}S$, and $^3H$. In other embodiments, the derivative has been labeled with fluorophores, chemiluminescent agents, enzymes, and antiligands that can serve as specific binding pair members for a labeled ligand.

In some embodiments, the methods of this invention use peptide analogs and mimetics which mimic the three-dimensional structure of an SLPI protein in lieu of SLPI proteins. Such peptide mimetics can compete with SLPI for NF-κB and serine protease inhibitory functions. Peptide mimetics may be superior to naturally-occurring peptides for a variety of reasons, including greater chemical stability, enhanced bioactivity and pharmacological properties (half-life, absorption, potency, efficacy, etc.), the potential for altered specificity (e.g., a broad-spectrum of biological activities), reduced antigenicity, and economic considerations with regard to production.

Generally, peptidomimetics are structurally similar to a paradigm polypeptide (i.e., a polypeptide that has a desired biochemical property or pharmacological activity), but have one or more peptide linkages optionally replaced by a linkage selected from the group consisting of: —$CH_2NH$—, —$CH_2S$—, —$CH_2$—$CH_2$—, —$CH$═$CH$— (cis and trans), —$COCH_2$—, —$CH(OH)CH_2$—, and $BCH_2SO$—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch, Ann. Rev. Biochem. 61:387 (1992)), for example, by adding internal cysteine residues capable of forming intramolecular disulfide bridges which cyclize the peptide.

In one embodiment, mimetics of the invention are peptide-containing molecules that mimic elements of protein secondary structure by orienting chemical structural motifs to facilitate desired molecular interactions similar to the natural molecule (see, e.g., Johnson et al., (1993) Peptide Turn Mimetics, in Biotechnology and Pharmacy, Pezzuto et al., (editors) Chapman and Hall).

In another embodiment, peptide analogs of the invention are non-peptide compounds with properties analogous to those of a template peptide, also referred to as "peptide mimetics" or "peptidomimetics" and may be developed with the aid of computerized molecular modeling, as described (see, e.g., Fauchere, (1986) Adv. Drug Res. 15, 29-69; Veber & Freidinger, (1985) Trends Neurosci. 8, 392-396; Evans et al., (1987) J. Med. Chem. 30, 1229-1239, which are incorporated herein by reference).

In some embodiments, the methods of this invention use agonists of SLPI proteins and positive regulators of the SLPI protein or gene (including those that can up-regulate SLPI transcription in a mammal) in lieu of SLPI proteins.

Methods of Using SLPIs

The present invention provides a method of treating or preventing damage to nervous tissue or neurons comprising the step of administering, in a manner which can affect the nervous system, an SLPI molecule of this invention. Also provided are methods of promoting neural regeneration to nervous tissue or neurons comprising the step of administering, in a manner which can affect the nervous system, an SLPI molecule of this invention. In a preferred embodiment, the damage results from peripheral nerve injury or neuropathy, cranial or cerebral trauma, aneurysm, spinal cord injury or stroke.

The present invention also provides a method of treating or preventing neural degeneration or damage associated with a disorder, disease or condition comprising the step of administering, in a manner which can affect the nervous system, an SLPI molecule. Also provided are methods of promoting neural regeneration to nervous tissue or neurons associated with a disorder, disease or condition comprising the step of administering, in a manner which can affect the nervous system, an SLPI molecule of this invention. In a preferred embodiment, the disorder, disease or condition is associated with apoptosis. In another preferred embodiment, the disorder, disease or condition results from a demyelinating disease. Diseases which may be treated include, but are not limited to: Alzheimer's disease, Parkinson's disease, Creutzfeldt-Jacob disease, kuru, Huntington's disease, multiple system atrophy, amyotropic lateral sclerosis (Lou Gehrig's disease), progressive supranuclear palsy, and demyelinating diseases including multiple sclerosis, monophasic demyelination, encephalomyelitis, multifocal leukoencephalopathy, panencephalitis, Marchiafava-Bignami disease, pontine myelinolysis, adrenoleukodystrophy, Pelizaeus-Maerzbacher disease, Spongy degeneration, Alexander's disease, Canavan's disease, metachromatic leukodystrophy, Krabbe's disease, spinal motor atrophy, Charcot-Marie-Tooth diseases, and eye diseases such as optic neuritis, diabetic retinopathy, macular degeneration, and glaucoma.

The present invention also provides a method of treating or preventing neural degeneration or damage associated with a disorder, disease or condition comprising the step of administering, in a manner which can affect the nervous system, a neuron which has been exposed to an SLPI molecule. Also provided are methods of promoting neural regeneration to nervous tissue or neurons associated with a disorder, disease or condition comprising the step of administering, in a manner which can affect the nervous system, a neuron which has been exposed to an SLPI molecule. In one embodiment, the neuron is exposed ex vivo (e.g., in culture) to an SLPI molecule of the invention.

Methods of Stimulating Neuronal Regeneration by Targeting Proteins Regulated by SLPIs This invention also provides methods of decreasing the expression or activity of a protein in a neuron that is down-regulated by SLPI, thereby achieving equivalent neuronal stimulation as done by supplying SLPI. For example, instead of supplying SLPIs to the neuronal site in need of treatment, one can decrease the expression or activity of apoptosis-related proteins such as (1) proinflammatory cytokines (e.g., TNF-$\alpha$ and TNF-$\beta$); (2) stress response genes such as superoxide dismutase (Cu/Zn and Mn); and (3) pro-apoptotic factors such as Bax, caspases (e.g., caspase-11), and TRAF-1 and 2. In other embodiments, one can decrease the expression or activity of proteins related to myelin inhibition of axonal growth such as (1) growth factor receptors (e.g., EGFR); (2) certain enzymes such as BACE (beta site amyloid precursor protein cleaving enzyme, a member of a family of enzymes recently shown to be involved in cleavage of the p75 receptor, an event that is required for inhibition; (3) protein kinase C delta; and (4) myelin proteins (e.g., myelin basic protein). In still other embodiments, one can decrease the expression or activity of proteins related to Alzheimer's disease such as $\beta$-amyloid and apolipoprotein E.

Identification of Useful SLPIs

SLPIs useful in this invention can be identified through neurite outgrowth assays. Neurite outgrowth assays may be performed, for example, using cultured neurons in the presence of purified myelin. See, e.g., GrandPre et al., Nature 417:547-551 (2002); see also Norton and Poduslo, J. Neurochem. 21:749-757 (1983) for myelin preparations. Alternatively, neurite outgrowth assays may be performed on a growth permissive substrate, e.g., on a monolayer of transfected cells (e.g., COS or CHO cells) that are engineered to express cell surface neural inhibitory molecules, such as MAG (see, e.g., Domeniconi et al., Neuron 35:283-290 (2002); WO 97/01352); OMgp (see, e.g., Wang et al., Nature 417:941-944 (2002); or cells that express NgR or NgR derivatives (see, e.g., Domeniconi et al., Neuron 35:283-290 (2002); Liu et al., Science 297:1190-1193 (2002); Wang et al., Nature 417:941-944 (2002); GrandPre et al., Nature 417: 547-551 (2002)). Additional methods known in the art may also be used to assay neurite outgrowth.

Methods of Producing SLPI Polypeptides

The present invention provides expression vectors encoding SLPI polypeptides, where the SLPI-coding sequences are operatively linked to an expression control sequence. A wide variety of host/expression vector combinations may be employed. Useful expression vectors, for example, may comprise segments of chromosomal, non-chromosomal and synthetic nucleic acid sequences. Useful expression vectors for bacterial and eukaryotic host cells, such as yeast or mammalian cells, may be used. Expression in mammalian cells, for example, can be achieved using a variety of plasmids, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL941. (See below for a more detailed discussion on gene delivery using viral vectors).

In addition, any of a wide variety of expression control sequences may be used in these vectors to express the DNA sequences of this invention. Expression control sequences that control transcription include, e.g., promoters, enhancers and transcription termination sites. Expression control sequences in eukaryotic cells that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct targeted expression of the polypeptide to or within particular cellular compartments, and sequences in the 5' and 3' untranslated regions that modify the rate or efficiency of translation and/or mRNA degradation.

Many examples of useful expression control sequences—including constitutive, inducible and tissue-specific promoter and/or enhancer sequences—are known to control the expression of genes of prokaryotic or eukaryotic cells and their viruses. Promoters suitable for use with prokaryotic hosts include the regulated beta-lactamase, lactose, tryptophan (trp) and lambda phage promoter systems, alkaline phosphatase, and hybrid promoters such as the tac promoter. Promoters for use in bacterial systems will preferably contain a Shine-Dalgarno (S.D.) sequence operably linked to the DNA encoding the polypeptide of interest. Examples of suitable promoters for use in yeast hosts include the promoters for 3-phosphoglycerate kinase or other glycolytic enzymes. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

Transcription from vectors in mammalian host cells may be controlled, for example, by promoters obtained from the genomes of viruses such as polyoma virus, fowlpox virus, adenovirus (such as Adenovirus 2 or 5), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems. Other useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage 1, the control regions for fd coat protein, the promoter for 3-phosphoglycerate kinase or other glycolytic enzymes, the promoters of acid phosphatase, e.g., PhoS, the promoters of the yeast a-mating factors, the polyhedron promoter of the baculovirus system and other sequences known to control the expression of genes of prokaryotic or eukaryotic cells or their viruses, and various combinations thereof.

Transcription of a DNA encoding a polypeptide of the invention by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus (CMV) immediate early promoter/enhancer, the polyoma enhancer on the late side of the replication origin, and adenovirus enhancers. The enhancer may be spliced into the vector at a position 5' or 3' to the coding sequence of interest, but is preferably located at a site 5' from the promoter.

In a preferred embodiment, the promoter and/or regulatory sequences are designed specifically for expression (preferably regulated expression) in a cell of the nervous system, e.g., a neural or glial cell. In a more preferred embodiment, the promoter is a neural specific promoter, e.g., a neural specific enolase promoter. Other neural specific promoters are known in the art (see, e.g., U.S. Pat. Nos. 6,066,726 and 5,753,502). Thus, in a preferred embodiment, the nucleic acid of the invention is operably linked to at least one transcriptional regulatory sequence which is useful for treating or preventing an injury, condition or disease in a patient characterized by diminished potential for axonal growth.

Expression vectors used in eukaryotic host cells (yeast, fungi, insect, plant, animal, human, or nucleated cells from other multicellular organisms) will preferably also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide of the invention.

Preferred nucleic acid vectors also include a selectable and optionally, an amplifiable marker gene (e.g., DHFR) and means for amplifying the copy number of the gene of interest. Such marker genes are well-known in the art. Nucleic acid vectors may also comprise stabilizing sequences (e.g., ori- or ARS-like sequences and telomere-like sequences), or may alternatively be designed to favor directed or non-directed integration into the host cell genome.

In a preferred embodiment, nucleic acid sequences of this invention are inserted in frame into an expression vector that allows high level expression of an RNA which encodes a protein comprising the encoded nucleic acid sequence of interest. Nucleic acid cloning and sequencing methods are well known to those of skill in the art and are described in an assortment of laboratory manuals, including Sambrook et al., supra; and Ausubel et al., supra. Product information from manufacturers of biological, chemical and immunological reagents also provide useful information.

Of course, not all vectors and expression control sequences will function equally well to express the nucleic acid sequences of this invention. Neither will all hosts function equally well with the same expression system. However, one of skill in the art may make a selection among these vectors, expression control sequences and hosts without undue experimentation and without departing from the scope of this invention. In selecting an expression control sequence, a variety of factors should also be considered. These include, for example, the relative strength of the sequence, its controllability (e.g., regulatable inducible expression, etc.), and its compatibility with the nucleic acid sequence of this invention, particularly with regard to potential secondary structures. The design of the expression vector may also depend on such factors as the choice of the host cell to be transformed and/or the type of protein desired to be expressed. Moreover, the copy number and ability to control the copy number of the vector and the expression of any other proteins encoded by the vector, such as markers, should also be considered.

Unicellular hosts (e.g., bacteria, yeasts, and animal or plant cells in culture) should be selected by consideration of their compatibility with the chosen vector, the toxicity of the product coded for by the nucleic acid sequences of this invention, their secretion characteristics, their ability to fold the polypeptide correctly, their fermentation or culture requirements, and the ease of purification from them of the products coded for by the nucleic acid sequences of this invention.

Suitable host cells for the expression of polypeptides of the invention are derived from multicellular organisms. Examples of invertebrate cells include insect cells such as *Drosophila* S2 and *Spodoptera* Sf9, as well as plant cells. Examples of useful mammalian host cell lines include but are not limited to Chinese hamster ovary (CHO) and COS cells. Other examples include monkey kidney CV1 line transformed by SV40 (COS-7, ATCC CRL 1651); human embryonic kidney line (293 or 293 cells selected for growth in suspension culture); CHO cells lacking a functional DHFR gene (e.g., Urlaub and Chasin, Proc. Natl. Acad. Sci. USA, 77:4216 (1980)); mouse sertoli cells (e.g., TM4); human lung cells (W138, ATCC CCL 75); human liver cells (e.g., Hep G2, BB 8065); and mouse mammary tumor cells (e.g., MMT 060562, ATCC CCL51). Human stem cells (see, e.g., U.S. Pat. Nos. 6,245,566 and 6,090,622) and particularly neural stem cells and associated delivery systems (see, e.g., U.S. 20020164309 and 20020064873) may also be used in accordance with the invention. The selection of appropriate host cells takes into consideration the vector on which the nucleic acid of the invention is carried and is within the skill in the art.

Transformation and other methods of introducing nucleic acids into a host cell (e.g., conjugation, protoplast transformation or fusion, transfection, electroporation, liposome delivery, membrane fusion techniques, high velocity DNA-coated pellets, viral infection and protoplast fusion) can be accomplished by a variety of methods which are well known in the art (see, for instance, Ausubel, supra, and Sambrook et al., supra). Depending upon the host cell, vector, and method of transformation used, transient or stable expression of the polypeptide will be constitutive or inducible. One having ordinary skill in the art will be able to decide whether to express a polypeptide transiently or in a stable manner, and whether to express the protein constitutively or inducibly.

Particular details of the transfection, expression and purification of recombinant proteins are well documented and are understood by those of skill in the art. Further details on the various technical aspects of each of the steps used in recombinant production of foreign genes in bacterial cell expression systems can be found in a number of texts and laboratory manuals in the art. See, e.g., Ausubel et al., supra, and Sambrook et al., supra, and Kieser et al., supra, herein incorporated by reference.

Pharmaceutical Compositions and Treatments

The SLPIs of this invention may be formulated into pharmaceutical compositions and administered in vivo at an effective dose to treat the particular clinical condition addressed. Administration of one or more of the pharmaceutical compositions according to this invention will be useful for regulating and for promoting neural growth or regeneration in the nervous system, for treating injuries or damage to nervous tissue or neurons, and for treating neural degeneration associated with traumas to the nervous system, disorders, conditions or diseases. Such traumas, conditions, diseases, disorders or injuries include, but are not limited to: cranial or cerebral trauma, aneurysms, strokes, spinal cord injury, Alzheimer's disease, Parkinson's disease, Creutzfeldt-Jacob disease, kuru, Huntington's disease, multiple system atrophy, amyotropic lateral sclerosis (Lou Gehrig's disease), progressive supranuclear palsy, and demyelinating diseases including multiple sclerosis, monophasic demyelination, encephalomyelitis, multifocal leukoencephalopathy, panencephalitis, Marchiafava-Bignami disease, pontine myelinolysis, adrenoleukodystrophy, Pelizaeus-Maerzbacher disease, Spongy degeneration, Alexander's disease, Canavan's disease, metachromatic leukodystrophy, Krabbe's disease, spinal motor atrophy, and Charcot-Marie-Tooth diseases.

The compositions of this invention may be administered alone or in combination with one or more therapeutic or diagnostic agents. For example, the compositions of this invention may be administered together with but not limited to, e.g., anti-inflammatory agents, anticoagulants, antithrombotics, or tissue plasminogen activators.

The patient to be treated may be a human or a veterinary animal. Determination of a preferred pharmaceutical formulation and a therapeutically efficient dose regiment for a given application is within the skill of the art taking into consideration, for example, the condition and weight of the patient, the extent of desired treatment and the tolerance of the patient for the treatment.

Administration of the SLPIs of this invention, including isolated and purified forms, their salts or pharmaceutically acceptable derivatives thereof, may be accomplished using any of the conventionally accepted modes of administration of agents which are used to treat neuronal injuries or disorders. In one embodiment, autologous, allologous, or heterologous cells which have been engineered to express one or more SLPI molecules of the invention may be used in therapeutic treatment regimes. Such engineered cells may be used to synthesize a therapeutic agent which can then be administered independently to a host. Alternatively, cells transformed, transfected, or infected with exogenous nucleic acid such as DNA or RNA that expresses an SLPI molecule of the invention that is secreted or released from the engineered cell may be used directly as a therapeutic, e.g., by implanting such engineered cells into a host at a region which is in communication with the targeted tissue or cells in need of treatment.

If the polypeptide of the invention is not normally a secreted protein, it can be engineered to possess a signal peptide required for secretion of a protein from a host cell. Such signal peptides are characterized by their length (about 16-30 amino acids) and hydrophobicity and which are not highly conserved at the amino acid sequence level (see, e.g., Lodish et al., Molecular Cell Biology, 3d ed., Scientific American Books, W.H. Freeman and Company, New York, 1995, Chapter 16). Amino acid residues which function as a signal sequence for secretion in a eukaryotic cell may be engineered onto the N-terminus of a heterologous protein by any of a number of routine genetic engineering methods well known to those of skill in the art See, e.g., Farrell et al., Proteins, 41, pp. 144-53 (2000) (see also http://www.healthtech.com/2001/pex); Borngraber et al., Protein Expr. Purif., 14, pp. 237-46 (1998); Collins-Racie et al., Biotechnology, 13, pp. 982-987 (1995); U.S. Pat. No. 5,747,662; WO00/50616; WO99/53059; and WO96/27016; each of which is incorporated herein by reference in its entirety. Host cells which express a secreted form of a polypeptide of the invention would be expected to elevate levels of that polypeptide in the cerebrospinal fluid (CSF) which bathes the nervous system. Alternatively, it is possible to provide a molecule of the invention, e.g., by injection, directly to the CSF. Transfected cells, secreting other forms of a molecule of the invention, may be administered to a site of neuronal injury or degeneration in a similar manner.

Viral or non-viral gene delivery into cells which then overexpress an SLPI molecule of the invention may be performed ex vitro or in vivo by any of a number of techniques well known to those of skill in the art. A number of such delivery methods have been shown to work with neurons. See, e.g., US 20020168760 (Retroviral vectors for gene transfer into neuronal cells); US 20020168338 (DNA delivery to the central nervous system); Cherksey et al., U.S. Pat. No. 6,210,664 (Method for gene transfer to the central nervous system involving a recombinant retroviral expression vector); Kaplitt et al., U.S. Pat. No. 6,180,613 (AAV-mediated delivery of DNA to cells of the nervous system); Hayes et al., U.S. Pat. No. 6,096,716 (Liposome-mediated transfection of central nervous system cells); Kochanek et al, U.S. Pat. No. 5,981,225 (Gene transfer vector, recombinant adenovirus particles containing same, method for producing the same and method of use of the same); Gage et al., U.S. Pat. No. 5,762,926 (Method of grafting genetically modified cells to treat defects, disease or damage to the central nervous system); WO/008192 (Herpes viral vectors for gene delivery); and CA2247912 (Genetically engineered primary oligodendrocytes for transplantation-mediated gene delivery in the central nervous system); the entire disclosures of which are incorporated herein by reference.

For example, neuronal cells can be infected with a viral vector which causes the infected host cells to express a molecule (e.g., a polypeptide) of the invention at high levels. Useful viral vectors, include, without limitation, recombinant retroviruses, adenovirus, adeno-associated virus, and herpes simplex virus-1, or other attenuated viruses, or recombinant bacterial or eukaryotic plasmids which can be taken up by a damaged axon. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or calcium phosphate precipitation carried out in vivo. The choice of a particular nucleic acid delivery system will depend on such factors as the intended target and the route of administration, e.g. locally or systemically. In a preferred embodiment, a vector construct is used in such a way that the expression product can cross the blood brain barrier. Furthermore, it will be recognized that vectors enabling in vivo regulation of expression are also useful for in vitro modulation of expression in cells, such as for use in ex vivo assay systems such as those described herein.

One preferred viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, e.g., Berkner et al. *BioTechniques* 6:616 (1988); Rosenfeld et al. *Science* 252:431-434 (1991); and Rosenfeld et al. *Cell* 68:143-155 (1992). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types (Rosenfeld et al. supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham J. Virol. 57:267 (1986)). Most replication-defective adenoviral vectors currently in use and therefore favored by the present invention are deleted for all or parts of the viral E1 and E3 genes but retain as much as 80% of the adenoviral genetic material (see, e.g., Jones et al. *Cell* 16:683 (1979); Berkner et al., supra; and Graham et al. in Methods in Molecular Biology, E. J. Murray, Ed. (Humana, Clifton, N.J., 1991) vol. 7. pp. 109-127). Expression of the inserted nucleic acid sequences can be under control of, for example, the E1A promoter, the major late promoter (MLP) and associated leader sequences, the E3 promoter, or exogenously added promoter sequences.

Another preferred viral vector system useful for delivery of the nucleic acid molecule of the invention is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. Curr. Topics in Micro. and Immunol. 158: 97-129 (1992)). It is also one of the few viruses that may integrate its DNA into non-dividing cells, and exhibits a high frequency of stable integration (see for example Flotte et al. Am. J. Respir. Cell. Mol. Biol. 7:349-356 (1992); Samulski et al. J. Virol. 63:3822-3828 (1989); and McLaughlin et al. J. Virol. 62:1963-1973 (1989)). A variety of nucleic acids have been introduced into different cell types using AAV vectors (see for example Hermonat et al. Proc. Natl. Acad. Sci. USA 81:6466-6470 (1984); Tratschin et al. Mol. Cell. Biol. 4:2072-2081 (1985); Wondisford et al. Mol. Endocrinol. 2:3239 (1988); Tratschin et al. J Virol. 51:611-619 (1984); and Flotte et al. J. Biol. Chem. 268:3781-3790 (1993)).

Yet another preferred viral vector system useful for delivery of the nucleic acid molecule of the invention is a replication defective Herpes simplex virus-1 (HSV-1) vector, which has been shown to achieve efficient transduction and expression of heterologous genes in the nervous system (Dobson et al. Neuron. 5:353 (1990); Federoff et al. Proc. Natl. Acad. Sci. U.S.A. 89:1636 (1992); Andersen et al. Hum Gene Ther. 3:487 (1992); Huang et al. Exp Neurol. 115:303 (1992); Fink et al. Hum Gene Ther. 3:11 (1992); Breakefield et al. in Gene Transfer and Therapy in the Nervous System. Heidelberg, F R G: Springer-Verlagpp 45-48 (1992); and Ho et al. Proc Natl. Acad. Sci. U.S.A. 90:3655 (1993)). HSV-2 vectors have also been described (Linnik et al. Stroke. 26:1670 (1995); Lawrence et al. J. Neuroscience. 16:486 (1996)).

Retrovirus vectors and adeno-associated virus (AAV) vectors are preferred vectors according to the invention for gene therapy in humans. These vectors provide efficient delivery of genes into cells, and the transferred nucleic acids are stably integrated into the chromosomal DNA of the host. The development of specialized cell lines ("packaging cells") that produce replication-defective retroviruses are especially preferred for gene therapy applications (see, e.g., Miller, A. D. Blood 76:271 (1990)). Recombinant retrovirus may be constructed in which part of the retroviral coding sequence (gag, pol, env) has been replaced by nucleic acid encoding one of the subject receptors rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses may be found, e.g., in Current Protocols in Molecular Biology, Ausubel, F. M. et al. (eds.) Greene Publishing Associates, (1989), Sections 9.10-9.14 and other standard laboratory manuals. Representative examples of retroviruses include pLJ, pZIP, pWE and pEM which are well known to those skilled in the art. Representative examples of packaging virus lines for preparing both ecotropic and amphotropic retroviral systems include psi.Crip, psi.Cre, psi 2 and psi.Am. Retroviruses have been widely used to introduce a variety of genes into many different cell types in vitro and/or in vivo. Moreover, it is useful to limit the infection spectrum of retroviruses and retroviral-based vectors by modifying the viral packaging proteins on the surface of the viral particle (see, for example PCT publications WO93/25234 and WO94/06920; Roux et al. PNAS 86:9079-9083 (1989); Julan et al. J. Gen Virol 73:3251-3255 (1992); and Goud et al. Virology 163: 251-254 (1983)); Neda et al. J. Biol Chem 266:14143-14146 (1991)).

SLPIs can be delivered by spinal implantation (e.g., into the cerebrospinal fluid) of engineered cells or other biocompatible materials engineered to release or secrete such molecules according to this invention. Optionally, transfected cells that release or secrete one or more molecules or the invention may be encapsulated into immunoisolatory capsules or chambers and implanted into the brain or spinal cord region using available methods that are known to those of skill in the art. See, e.g., U.S. Pat. Nos. 6,179,826, 6,083,523; 5,676,943; 5,653,975; 5,487,739; 4,298,002; 4,670,014; and U.S. Pat. No. 5,487,739; WO 89/04655; WO 92/19195; WO93/00127; and references cited therein, all of which are incorporated herein by reference. Alternatively, a pump and catheter-like device may be used. A pump, such as one designed for subcutaneous administration, and/or a catheter-like device may be implanted at or inserted into the site of injury, e.g., subcutaneously or intrathecally, to administer an SLPI on a timely basis and at the desired concentration. See, e.g., U.S. Pat. No. 4,578,057 and references cited therein; for implantable pumps, see, e.g., http://www.medtronic.com); which are each incorporated herein by reference.

If the molecule of the invention is capable of crossing the blood brain barrier, it may be administered using a pump and catheter-like device implanted at or inserted at a location distant from the site of injury on a timely basis and at the desired concentration, which can be selected and empirically modified by one of skill in the art. If the molecule of the invention does not cross the blood brain barrier, it can be delivered intrathecally using a pump and catheter-like device either close to or at a distance from the lesion site.

The SLPIs of the invention may be administered, alone or in combination with one or more agents that provide an environment favorable to axonal growth, by a variety of means. In one embodiment, they may be incorporated into or administered in conjunction with a vector of the invention. In another embodiment, they may be injected, either locally or systemically, and are preferably co-administered with a molecule or composition of the invention. In yet another embodiment, such agents may be supplied in conjunction with nerve guidance channels as described in U.S. Pat. Nos. 5,092,871 and 4,955,892. Examples of classes of such agents include trophic factors, receptors, extracellular matrix proteins, or intrinsic factors. Exemplary trophic factors include but are not limited to NGF, BDNF, NT-3, -4, -5, or -6, CNTF, LIF, IGFI, IGFII, GDNF, GPA, bFGF, TGFb, and apolipoprotein E. Exemplary receptors include but are not limited to the Trk family of receptors. An exemplary extracellular matrix protein is laminin. Exemplary intrinsic factors include but are not limited to GAP-43 and ameloid precursor protein (APP). Exemplary adhesion molecules include but are not limited to NCAM and L1.

The pharmaceutical compositions of this invention may be in a variety of forms, which may be selected according to the preferred modes of administration. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The SLPI molecules of this invention may, for example, be placed into sterile, isotonic formulations with or without cofactors which stimulate uptake or stability. The formulation is preferably liquid, or may be lyophilized powder. For example, the SLPI molecules may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

The pharmaceutical compositions of this invention may also be administered using microspheres, liposomes, nanoparticles and nano- or micro-particulate delivery systems or sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773,319; EP 58,481), copolymers of L-glutamic acid and gamma ethyl-L-glutamate (Sidman et al., Biopolymers 22:547-56 (1985)); poly(2-hydroxyethyl-methacrylate) or ethylene vinyl acetate (Langer et al., J. Biomed. Mater. Res. 15: 167-277 (1981); Langer, Chem. Tech. 12:98-105 (1982)).

Liposomes containing SLPIs of the invention can be prepared by well-known methods (See, e.g. DE 3,218,121; Epstein et al., Proc. Natl. Acad. Sci. U.S.A. 82:3688-92 (1985); Hwang et al., Proc. Natl. Acad. Sci. U.S.A. 77:4030-34 (1980); U.S. Pat. Nos. 4,485,045 and 4,544,545). Ordinarily the liposomes are of the small (about 200-800 Angstroms) unilamellar type in which the lipid content is greater than about 30 mol. % cholesterol. The proportion of cholesterol is selected to control the optimal rate of SLPI molecule release.

The SLPIs of this invention may also be attached to liposomes, which may optionally contain other agents to aid in targeting or administration of the compositions to the desired treatment site. Attachment may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., J. Cell. Biochem. Abst. Suppl. 16E 77 (1992)).

The SLPIs of the present invention may also be delivered by nanoparticle delivery. Numerous nanoparticle delivery methods are know in the art, including but not limited to nanocapsules.

The following terms, unless otherwise indicated, shall be understood to have the following meanings:

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences (Pearson, 1990, (herein incorporated by reference). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., supra, page 9.51, hereby incorporated by reference. For purposes herein, "high stringency conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "non-peptide analog" refers to a compound with properties that are analogous to those of a reference polypeptide. A non-peptide compound may also be termed a "peptide mimetic" or a "peptidomimetic". See, e.g., Jones, (1992) Amino Acid and Peptide Synthesis, Oxford University Press; Jung, (1997) Combinatorial Peptide and Nonpeptide Libraries: A Handbook John Wiley; Bodanszky et al., (1993) Peptide Chemistry—A Practical Textbook, Springer Verlag; "Synthetic Peptides: A Users Guide", G. A. Grant, Ed, W. H. Freeman and Co., 1992; Evans et al. *J. Med. Chem.* 30:1229 (1987); Fauchere, *J. Adv. Drug Res.* 15:29 (1986); Veber and Freidinger *TINS* p. 392 (1985); and references sited in each of the above, which are incorporated herein by reference. Such compounds are often developed with the aid of computerized molecular modeling. Peptide mimetics that are structurally similar to useful peptides of the invention may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein. For instance, a mutein may have an increased or decreased serine protease activity A mutein has at least 70% overall sequence homology to its wild-type counterpart. Even more preferred are muteins having 80%, 85% or 90% overall sequence homology to the wild-type protein. In an even more preferred embodiment, a mutein exhibits 95% sequence identity, even more preferably 97%, even more preferably 98% and even more preferably 99% overall sequence identity. Sequence homology may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the left-hand direction is the amino terminal direction and the right hand direction is the carboxy-terminal direction, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences). In a preferred embodiment, a homologous protein is one that exhibits 60% sequence homology to the wild type protein, more preferred is 70% sequence homology. Even more preferred are homologous proteins that exhibit 80%, 85% or 90% sequence homology to the wild type protein. In a yet more preferred embodiment, a homologous protein exhibits 95%, 97%, 98% or 99% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, herein incorporated by reference).

The following six groups each contain amino acids that are conservative substitutions for one another:
1) Serine (S), Threonine (T);
2) Aspartic Acid (D), Glutamic Acid (E);
3) Asparagine (N), Glutamine (Q);
4) Arginine (R), Lysine (K);
5) Isoleucine (I), Leucine (L), Methionine (M), Alanine (A), Valine (V), and
6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A preferred algorithm when comparing an SLPI sequence to a database containing a large number of sequences from different organisms is the computer program BLAST, especially blastp or tblastn (Altschul et al., 1997, herein incorporated by reference). Preferred parameters for BLASTp are:
Expectation value: 10 (default)
Filter: seg (default)
Cost to open a gap: 11 (default)
Cost to extend a gap: 1 (default
Max. alignments: 100 (default)
Word size: 11 (default)
No. of descriptions: 100 (default)
Penalty Matrix: BLOWSUM62

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

As used herein the phrase "therapeutically effective amount" means an amount of a molecule of the invention, such that a subject shows a detectable improvement in neuronal survival, growth or regeneration after being treated under the selected administration regime (e.g., the selected dosage levels and times of treatment).

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Standard reference works setting forth the general principles of recombinant DNA technology known to those of skill in the art include Ausubel et al., CURRENT PROTOCOLS IN MOLECULAR BIOLOGY, John Wiley & Sons, New York (1998 and Supplements to 2001); Sambrook et al., MOLECULAR CLONING: A LABORATORY MANUAL, 2d Ed., Cold Spring Harbor Laboratory Press, Plainview, N.Y. (1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991). Standard reference works setting forth the general principles of immunology known to those of skill in the art include: Harlow and Lane ANTIBODIES: A LABORATORY MANUAL, 2d Ed., Cold Spring Harbor Laboratory Press, Cold Spring Harbor, N.Y. (1999); and Roitt et al., IMMUNOLOGY, 3d Ed., Mosby-Year Book Europe Limited, London (1993). Standard reference works setting forth the general principles of medical physiology and pharmacology known to those of skill in the art include: Harrison's PRINCIPLES OF INTERNAL MEDICINE, 14th Ed., (Anthony S. Fauci et al., editors), McGraw-Hill Companies, Inc., 1998.

Throughout this specification and paragraphs, the word "comprise" or variations such as "comprises" or "comprising", will be understood to imply the inclusion of a stated integer or group of integers but not the exclusion of any other integer or group of integers.

The following are examples which illustrate the compositions and methods of this invention. These examples should not be construed as limiting: the examples are included for the purposes of illustration only.

Example 1

Cerebellar neurons were isolated essentially as described in Doherty et al., Nature, 343, pp. 464-66 (1990); Neuron, 5, pp. 209-19 (1990); and Kleitman et al., Culturing Nerve Cells, pp. 337-78, MIT Press, Cambridge, Mass./London, England (G. Banker and K. Goslin, Eds.) (1991). Briefly, for animals up to nine days of age, the cerebellum was removed from two animals, and placed in 5 ml of 0.025% trypsin in PBS, triturated, and incubated for a further 10 minutes (min) at 37° C. Trypsinization was stopped by addition of 5 ml DMEM containing 10% fetal calf serum (FCS) and cells were centrifuged at 800 rpm for 6 min. The cells were resuspended to a single cell suspension in 2 ml of SATO containing 2% FCS.

Example 2

We previously established that there was a direct correlation between the level of cyclic AMP (cAMP) in neurons and inhibition of regeneration by myelin (see, e.g., WO 01/85981). Levels of endogenous cAMP were high in newborn neurons and extensive growth was observed on MAG and myelin, but at four days after birth, there was a precipitous drop in neuronal cAMP and this coincided with the onset of myelin inhibition. When cAMP levels in older neurons were elevated by treatment with dibutyrl cAMP (dbcAMP), inhibition was reversed and nerve fiber growth on MAG and myelin was enhanced. In vivo, cAMP levels could be elevated by lesioning a peripheral nerve or dbcAMP injection, and this led to regeneration of transected nerve fibers in the spinal cord.

The effects of cAMP were the result of its ability to induce gene transcription. To identify genes that were up-regulated, we performed microarray analysis on DRG neurons that received either dbcAMP or conditional lesion. We found that the expression of SLPI was greatly increased in both cases. We demonstrated in culture that nerve fiber growth on MAG and myelin was significantly increased when neurons were treated with SLPI and that this effect was equivalent to that seen with dbcAMP.

In addition, we found that SLPI increased the growth capacity of neurons when it was administered to adult animals. SLPI was delivered to the spinal cord by a pump. When the neurons were removed and plated on cells expressing MAG, growth was significantly increased. These data showed that SLPI has the potential to promote regeneration following CNS injury and in diseases characterized by axonal degeneration.

Figure 1B:
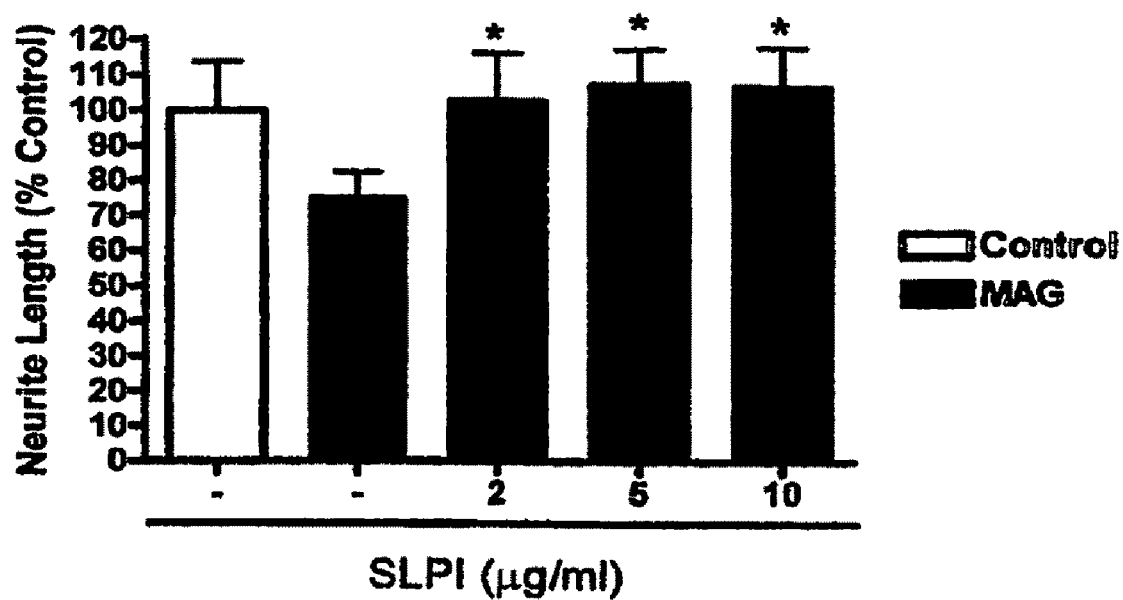

FIGS. 1A and 1B show that SLPI reversed inhibition by MAG for DRG neurons. Neurite outgrowth was strongly inhibited when untreated DRG neurons were plated on MAG-expressing CHO cells. However, when neurons were treated with SLPI, neurite outgrowth on MAG was significantly increased, with 5 and 10 μg/ml SLPI producing the most extensive growth.

Figure 2A:
FIGS. 2A and 2B are a panel of four photographs and a bar graph, respectively, showing that SLPI enhances neurite outgrowth on myelin for cortical neurons. Cortical neurons from post-natal day 1 rats were treated with 1 mM dibutyrl cAMP (dbcAMP) and 5 or 10 µg/ml SLPI, and plated onto 8-well chamber slides coated with central nervous system myelin (1 µg per well). Neurons were incubated for 24 hours and immunostained for βIII tubulin. The bar graph depicts average neurite length ±SEM.
Figure 2B:
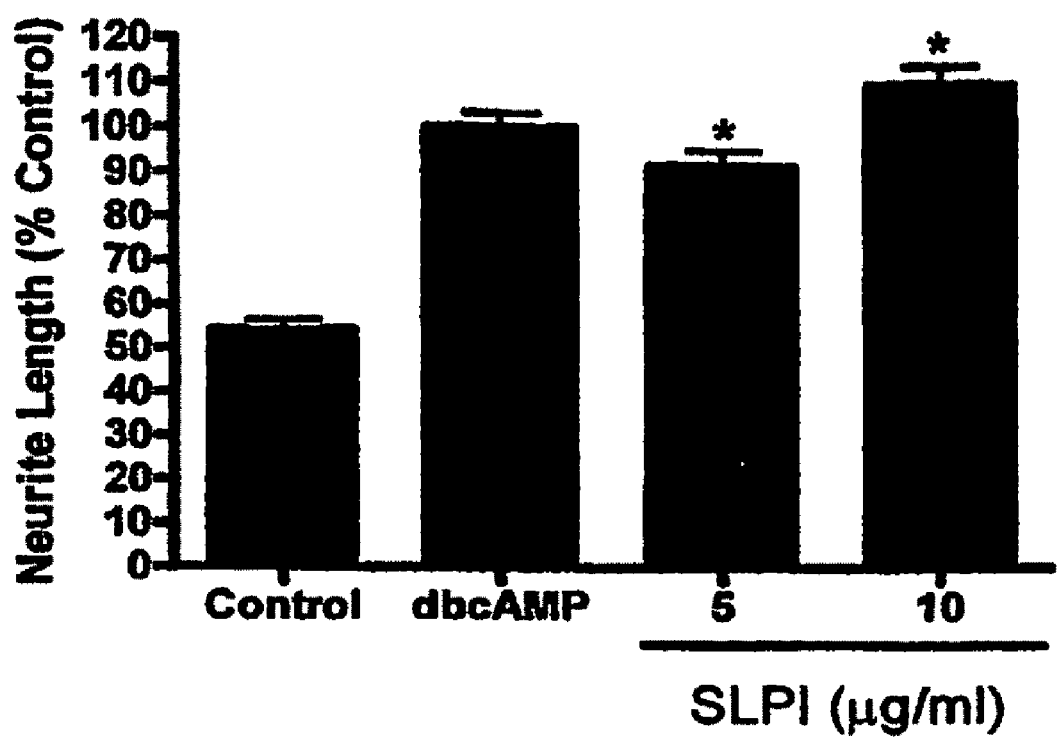

FIGS. 2A and 2B show that SLPI enhanced neurite outgrowth on myelin for cortical neurons. Unlike DRG neurons, cortical neurons were inhibited by MAG and myelin at postnatal day 1. Neurite outgrowth on myelin was significantly increased with 5 and 10 μg/ml SLPI and the effect was equivalent to that seen with dibutyryl AMP (dbcAMP).

Figure 3A:
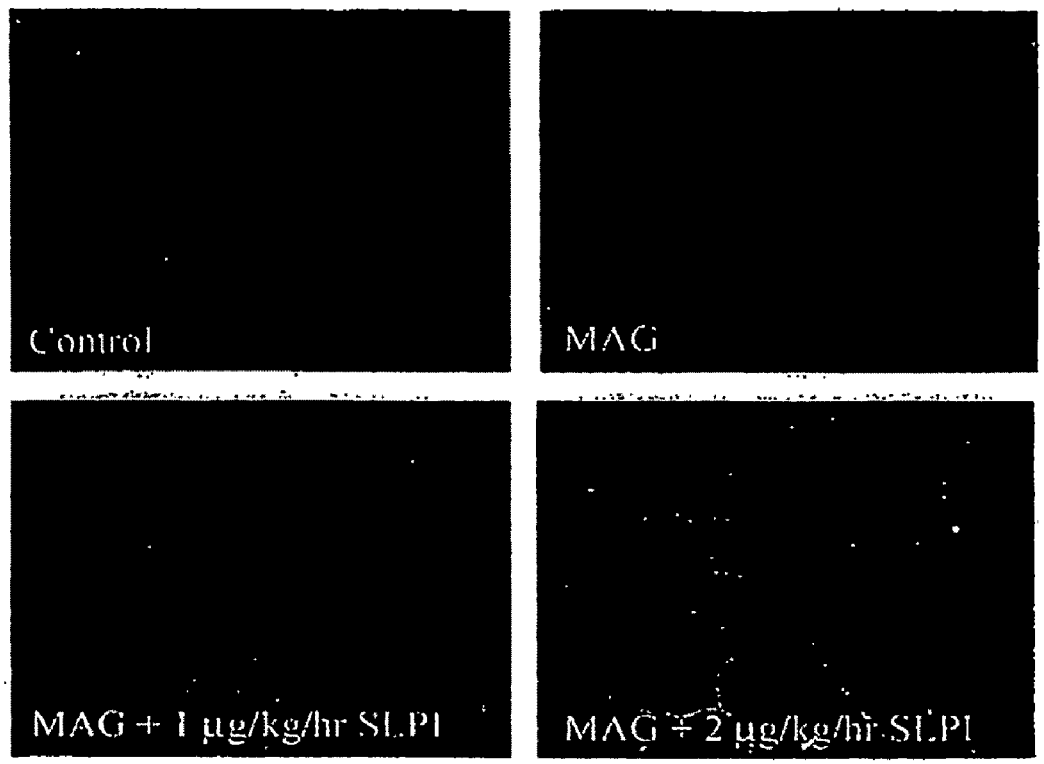
FIGS. 3A and 3B are a panel of four photographs and a bar graph, respectively, showing that in vivo delivery of SLPI overcomes MAG inhibition for adult DRG neurons. DRG neurons from adult rats that received infusion of 1, 2, or 5 µg/kg/hr SLPI into the spinal cord for 24 hours were plated onto control or MAG-expressing CHO cells. Neurons were incubated for 16 hours and stained for βIII tubulin. The bar graph depicts average neurite length ±SEM.
Figure 3B:
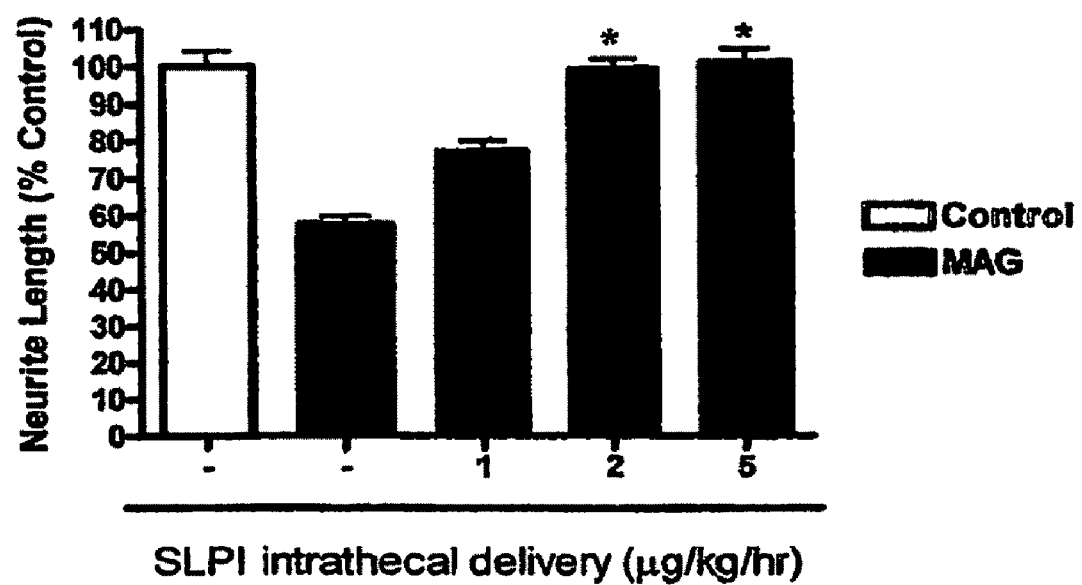
Figure 4:
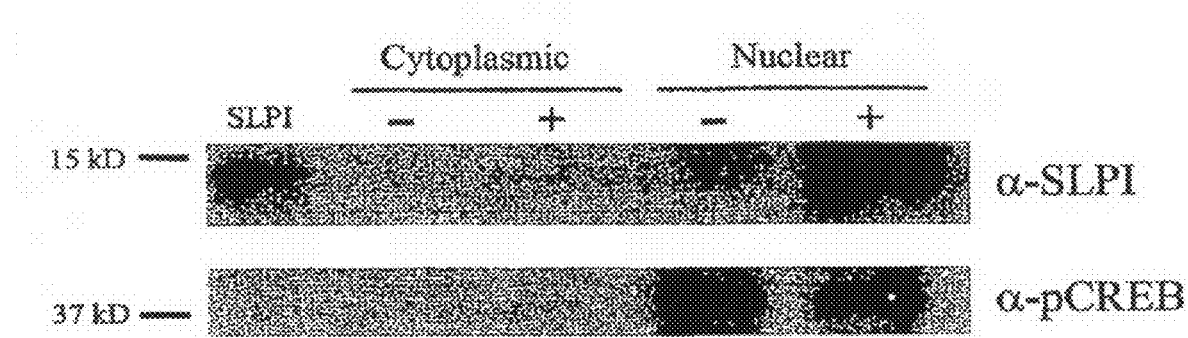
FIG. 4 is a Western blot image showing that SLPI localizes to the nuclei of cerebellar granule neurons ("CGN"). CGN from post-natal day 5 rats were incubated with 10 μg/ml SLPI for 1 hour. Cytoplasmic and nuclear fractions were isolated from untreated (−) and SLPI-treated (+) neurons and analyzed by Western blotting for SLPI. Membranes were also stripped and probed for phospho-CREB, an active transcription factor found in the nucleus, to verify the purity of the nuclear fractions. Recombinant SLPI was used as a positive control.

FIGS. 3A and 3B show that in vivo delivery of SLPI overcame MAG inhibition for adult DRG neurons. Intrathecal delivery of SLPI at rates of 2 and 5 μg/kg/hr blocks MAG inhibition for DRG neurons, leading to significant increases in neurite outgrowth. This indicated that SLPI was effective when administered to live animals.

In sum, the above results are the first to demonstrate that SLPI could overcome the inhibitory effects of MAG and myelin and promote axonal growth. The data showing that cortical neurite outgrowth is enhanced by SLPI are particularly significant because the axons of these neurons form the tracts that control motor function in the spinal cord. Most importantly, neurite outgrowth is increased following intrathecal delivery of SLPI to adult rats. These experiments provided evidence that SLPI may enhance the regenerative capacity of mature neurons when administered in vivo, making SLPI a viable therapeutic option for the treatment of spinal cord injury and other CNS trauma.

Example 3

As shown above, SLPI promotes growth when it is administered to live animals and it is non-toxic. To investigate the intracellular distribution of SLPI in CNS neurons, cerebellar granule neurons (CGN) were treated with recombinant SLPI for one hour and the proteins within the nuclei were separated from those in the cytoplasm. Western blotting was performed to detect SLPI in the nuclear and cytoplasmic fractions. To ensure that no endogenous SLPI was detected, we used an antibody raised against the recombinant SLPI in these experiments. We found that SLPI rapidly localized to the nucleus. SLPI was only present in the nuclear fraction isolated from SLPI-treated CGN, and the presence of phospho-CREB confirmed that SLPI localized to the nucleus.

In sum, we show for the first time that SLPI localizes to the nuclei of CGN. Thus, without being bound by theory, SLPI likely acts as a transcriptional regulator in neurons and promote axonal regeneration and neuronal survival by down-regulating the expression of genes that are involved in cell death (e.g., apoptosis) and myelin inhibition. These effects will be applicable not only to spinal cord injury, stroke and other CNS trauma, but also neurodegenerative disorders such as Alzheimer's disease, Parkinson's disease, amyotrophic lateral sclerosis, Huntington's disease, and multiple sclerosis.

Example 4

As shown above in Example 2, SLPI is effective when administered in vivo. To further confirm that SLPI can overcome myelin inhibition and encourage axonal regeneration following injury, dorsal column transections can be performed in adult rats. SLPI is then delivered intrathecally following dorsal column transection in adult rats. At an appropriate post-surgical timepoint, the spinal cord is examined histologically for evidence of dorsal column regeneration. Moreover, SLPI can be delivered intrathecally following ventral root or sciatic nerve transection in adult rats to evaluate regeneration of motor axons. Behavioral analysis is performed to measure recovery of motor function.

This approach can be applied to ALS by promoting motor axon regeneration following sciatic nerve and ventral root injury. Intrathecal delivery of SLPI is in conjunction with implantation of embryonic stem cell-derived motor neurons to encourage growth of motor axons through the ventral root exit zone. Similar experiments may be performed on embryonic or pre-adult rats to determine the effect of SLPI treatment at different developmental stages.

Example 5

Expression of TNF-α and TNF-α-mediated activation of p38 mitogen-activated protein kinase (MAPK) are events that have been correlated with the onset and progression of motor neuron loss in transgenic mice expressing G93A mutant superoxide dismutase-1, a widely used model of ALS (Elliott, Mol. Brain. Res. 95:172-78 (2001); Tortarolo et al., Mol. Cell. Neurosci. 23:180-92 (2003); Yuasa et al., J. Biol. Chem. 273:22681-92 (1998). To determine whether SLPI can decrease INF-α levels and p38MAPK activation in neurons, one can use ELISA to measure levels of TNF-α in DRG neurons and CGN treated with SLPI for 1 hour in vitro. SLPI can also be delivered intrathecally to adult rats and ELISA analysis is performed on spinal cord tissue samples to determine if TNF-α levels are decreased in vivo. The ability of SLPI to block p38MAPK activation can be tested by pre-incubating neurons with SLPI and then treating with TNF-α. Phosphorylation of p38MAPK can be analyzed by Western blotting.

Example 6

As shown above, SLPI localizes to the nuclei of CGN. To confirm that treatment with SLPI affects transcription in neurons, one can perform chromatin immunoprecipitation (ChIP) experiments to identify other genes that are regulated by SLPI. This approach can yield new molecular targets to prevent motor neuron loss in models of ALS. In addition, promoters that interact with SLPI can be identified by ChIP analysis of SLPI-treated neurons and DNA sequencing. Candidate genes are identified based on their roles in cell death and myelin inhibition, and additional ChIP analysis and PCR can be carried out to evaluate the ability of SLPI to down-regulate their expression.

Example 7

To determine in vivo dosage and toxicity of SLPI, SLPI can be administered either intrathecally or subcutaneously in adults rats that have undergone dorsal column transections. Dorsal column lesion is selected because it is a relatively simple model of spinal cord injury that produces paralysis but preserves bladder function, greatly facilitating the animals' post-operative care. Axonal regeneration observed in the dorsal columns will provide proof SLPI's therapeutic potential.

Dose-response experiments to determine the optimal concentration of SLPI can be done as follows. P6 DRG and cerebellar neurons are treated with 0, 1, 2, 5, 10, 20 or 50 µg/ml SLPI. CHO cell monolayers and CNS myelin substrates are prepared in 8-well chamber slides. Neurons are plated at a density of about 10,000 neurons per well, incubated for 16-18 hrs, and immunostained for βIII tubulin. Neurite outgrowth is quantified as previously described (Mukhopadhyay et al., Neuron 13:757-67 (1994)).

SLPI is administered to adult rats through subcutaneous injection or intrathecal pumps. A control group receives saline by the same means. DRG neurons are dissociated, transferred to monolayers of control and MAG-expressing CHO cells, and cultured overnight. Neurite outgrowth is quantified as described above.

To create dorsal column lesions, dorsal column transactions are performed at T6-T7 in 8-week old female rats as described in Qiu et al., Neuron 34:895-903 (2002). The optimal concentration of SLPI is delivered via subcutaneous injection or intrathecal pumps that are inserted at the time of injury and removed at an appropriate time. Saline is administered as a control. On post-surgical day 24, axons are trans-ganglionically traced by injecting 4 ml of 1% biotinylated cholera toxin B-subunit (CTB) into the left sciatic nerve. Animals are sacrificed 4 days later by transcardial perfusion and the thoracic spinal cords are removed, post-fixed and cryoprotected. Spinal cords are longitudinally sectioned at 20 µm and immunostained for βIII tubulin. CTB is visualized by incubation with fluorescein-conjugated streptavidin and axonal regeneration is demonstrated by the co-localization of βIII tubulin and CTB.

Example 8

Neutrophils play a major role in the secondary neuronal damage that occurs in the early stages of spinal cord injury (Taoka et al., Neuroscience 79:1177-82 (1997); Carlson et al., Exp. Neurol. 151:77-88 (1998)). Large numbers of neutrophils infiltrate the injury site and release elastase, an SLPI substrate that specifically targets endothelial cells (Taoka et al., supra). To confirm that SLPI prevents neutrophil infiltration, hemorrhage, and neuronal necrosis after spinal cord injury, one can perform dorsal column lesions in rats and deliver SLPI to the animals as described above. One can also use a contusion model of injury as well. The animals are sacrificed at 1, 2, or 5 days after injury and the region of the spinal cord containing the lesion site is sectioned. These sections are stained with hemotoxylin and eosin and examined for evidence of hemorrhage and necrosis (Taoka et al., Brain Res. 799:264-69 (1998)). The extent of neutrophil infiltration and elastase expression is determined by immunostaining for myeloperoxidase and elastase, respectively. Finally, TUNEL staining in conjunction with immunostaining for βIII tubulin is performed to confirm the effects of SLPI on neuronal survival. A reduction in the number of necrotic neurons confirms that SLPI is an effective neuroprotective agent with the potential to greatly improve neurological outcome following acute spinal cord injury.

Example 9

To deliver the SLPI of the invention to animals, including humans, one can use a variety of methods that will be apparent to those of skill in the art, e.g., by standard techniques for delivery of molecules to the nervous system as well as by gene transfer techniques. Methods for viral or non-viral-mediated gene transfer into neurons and glial cells of the nervous system are known in the art. (See, e.g., Basic Science and Gene Therapy (2000) Cid-Arregui, A. and A. Garcia-Carranca, editors. Natick, Mass.: Eaton Publishing. SLPI molecules may be transferred into a desired target cell and expression products will appear in the fluids which bathe the cells of the nervous system, e.g., the CSF, which may then be transported into cells in communication with those fluids. Inducible and other regulated expression of polynucleotides of the invention are contemplated to be within the scope of this invention using known and available transcription control sequences and expression systems for regulating heterologous genes.

Mammalian cells (e.g., CHO or COS cells) transfected with an expression plasmid of the invention, e.g., one that encodes an expressed and secreted form of SLPI, are cultured and the cultures assayed for rate of secretion. The cells may be surgically implanted into the cerebrospinal fluid surrounding the spinal cord of a diseased or injured subject in the vicinity of nerve damage in need of repair.

Optionally, repeated administrations are performed. The cells secrete the SLPI and neural regeneration is stimulated.

Example 10

SLPI's ability to promote axonal regeneration in vivo in the optic nerve was investigated. Adult male Fischer rats (200-300 g, Charles River Laboratories) were anesthetized with isofluorane and placed in a stereotaxic frame. Optic nerve crush was performed as follows. The right optic nerve was exposed and the meninges were removed. The nerve was then crushed for 10 seconds with fine forceps at a distance of 2 mm behind the eye. Special care was taken to avoid injury to the opthalmic artery. After closing the incision, the animal received a single intravitreal injection of either 5 microliters sterile saline or 10 micrograms of recombinant human SLPI (R&D Systems; 2 micrograms/microliter in 5 microliters sterile saline) in the right eye. After a two-week post-surgical survival period, the animals were sacrificed by transcardial perfusion with 4% paraformaldehyde and the optic nerves were dissected. Nerves were sectioned at a thickness of 20 microns and thaw-mounted onto gelatin-coated slides. Sections were immunostained for GAP-43 using a polyclonal sheep anti-GAP-43 antibody diluted 1:1000 in a solution of 5% rabbit serum, 2% BSA, and 0.1% Tween in Tris-buffered saline (TBS). After an overnight incubation, the sections were rinsed in TBS and incubated in FITC-conjugated rabbit anti-sheep secondary antibody (1:500 in rabbit serum, BSA and Tween in TBS) for 2 hours at room temperature. Slides were coverslipped with Permafluor mounting medium (Thermo) and viewed under fluorescence.

Figure 5:
FIG. 5 are photographs showing GAP-43 staining of the optic nerve from an animal that received an injection of saline after the optic nerve crush (upper panel) or from an animal that received an injection of SLPI (lower panel).

Results are shown in FIG. 5. The upper panel shows the optic nerve of an animal that received an injection of saline after the optic nerve crush, while the lower panel is from an animal that received an injection of SLPI. GAP-43 is present only in actively growing axons, so the presence of GAP-43-positive axons is indicative of axonal growth and regeneration. No GAP-43 positive axons are present in the saline-treated nerve (FIG. 5, upper panel); however, there are numerous GAP-43 positive axons in the nerve that was treated with SLPI (FIG. 5, lower panel). There are many axons present at the site of injury and several of them extend beyond the lesion site (going from left to right in FIG. 5, lower panel), which is indicative of regenerating axons. Thus, these data show that treatment of injured optic nerves with SLPI leads to axonal growth and regeneration and further provide good indication that SLPI will be an effective means of promoting axonal regeneration in the CNS and in the optic nerve.

We claim:

1. A method of stimulating axonal outgrowth of a neuron, comprising contacting the neuron with SLPI, thereby stimulating said axonal outgrowth, and monitoring growth of the neuron after said contacting of the neuron with said SLPI.

2. A method of decreasing NF-κB or c-jun activity in a neuron, comprising contacting the neuron with SLPI, thereby decreasing said NF-κB or c-jun activity, and monitoring growth of the neuron after said contacting of the neuron with said SLPI.

3. A method of decreasing the inhibition of axonal outgrowth of a neuron by myelin, comprising contacting the neuron with SLPI, thereby decreasing said inhibition, and monitoring growth of the neuron after said contacting of the neuron with said SLPI.

4. The method of any one of claims 1-3, wherein the contacting step comprises contacting the cell body of the neuron.

5. The method of any one of claims 1-3, wherein the contacting step comprises contacting an axon of the neuron.

6. The method of any one of claims 1-3, wherein the neuron is injured.

7. The method of claim 6, wherein the neuron is in the spinal cord or in the peripheral nervous system.

8. The method of claim 6, wherein the neuron is a motor neuron.

* * * * *

UNITED STATES PATENT AND TRADEMARK OFFICE
CERTIFICATE OF CORRECTION

PATENT NO.       : 8,367,615 B2                                                       Page 1 of 1
APPLICATION NO. : 12/225639
DATED            : February 5, 2013
INVENTOR(S)      : Filbin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1073 days.

Signed and Sealed this

First Day of September, 2015

Michelle K. Lee
*Director of the United States Patent and Trademark Office*